(12) United States Patent
Gholap et al.

(10) Patent No.: US 10,338,365 B2
(45) Date of Patent: Jul. 2, 2019

(54) SLIDE STORAGE, RETRIEVAL, TRANSFER, AND SCANNING SYSTEM FOR A SLIDE SCANNER

(71) Applicant: OptraScan, Inc., Cupertino, CA (US)

(72) Inventors: Abhijeet Gholap, Cupertino, CA (US); Anagha Jadhav, Sunnyvale, CA (US); Isha Doshi, Sunnyvale, CA (US); Suraj Somwanshi, Sunnyvale, CA (US)

(73) Assignee: OPTRASCAN, INC., Cupertino, CA (US)

( * ) Notice: Subject to any disclaimer, the term of this patent is extended or adjusted under 35 U.S.C. 154(b) by 107 days.

(21) Appl. No.: 15/686,137

(22) Filed: Aug. 24, 2017

(65) Prior Publication Data

US 2018/0059395 A1 Mar. 1, 2018

Related U.S. Application Data

(60) Provisional application No. 62/378,812, filed on Aug. 24, 2016, provisional application No. 62/378,814, filed on Aug. 24, 2016.

(51) Int. Cl.
| | |
|---|---|
| *G02B 21/00* | (2006.01) |
| *G02B 21/34* | (2006.01) |
| *G02B 21/26* | (2006.01) |
| *G01N 35/04* | (2006.01) |
| *G02B 21/36* | (2006.01) |
| *G02B 21/24* | (2006.01) |
| *G06K 9/00* | (2006.01) |

(Continued)

(52) U.S. Cl.
CPC ........... *G02B 21/002* (2013.01); *G01N 35/04* (2013.01); *G02B 21/241* (2013.01); *G02B 21/26* (2013.01); *G02B 21/34* (2013.01); *G02B 21/365* (2013.01); *G06K 9/00134* (2013.01); *G01N 2035/00049* (2013.01); *G01N 2035/00089* (2013.01); *G01N 2035/00138* (2013.01); *G01N 2035/042* (2013.01); *G01N 2035/0425* (2013.01); *G06F 19/30* (2013.01); *G06T 2207/10056* (2013.01); *G06T 2207/30004* (2013.01)

(58) Field of Classification Search
CPC .... G02B 21/002; G02B 21/26; G02B 21/365; G02B 21/34; G02B 21/241; G01N 35/04; G01N 2035/00049; G01N 2035/0425; G01N 2035/042; G01N 2035/00138; G01N 2035/00089; G06K 9/00134; G06T 2207/10056; G06T 2207/30004; G06F 19/30
USPC ......................................................... 348/80
See application file for complete search history.

(56) References Cited

U.S. PATENT DOCUMENTS

| | | |
|---|---|---|
| 6,847,481 B1 | 1/2005 | Ludl et al. |
| 6,905,300 B1 * | 6/2005 | Russum ........... G01N 35/00029 406/86 |

(Continued)

*Primary Examiner* — Jared Walker

(57) ABSTRACT

A slide storage, retrieval, transfer and scanning system for a slide scanner presents multiple components which work together in an automated fashion to streamline slide scanning in digital pathology. A slide storage assembly stores several slide baskets and can deliver a particular basket through a rotation mechanism. A slide basket transfer assembly retrieves the basket from the slide storage assembly and transfers the basket to a secondary location, where a slide transfer assembly retrieves a single slide from the basket and delivers the slide to a slide scanning stage for scanning.

15 Claims, 9 Drawing Sheets

(51) Int. Cl.
 *G06F 19/00* (2018.01)
 *G01N 35/00* (2006.01)

(56) References Cited

U.S. PATENT DOCUMENTS

| | | |
|---|---|---|
| 7,706,061 B2 | 4/2010 | Tafas |
| 2008/0187464 A1 | 8/2008 | Guo et al. |
| 2014/0178169 A1* | 6/2014 | Hebert ...................... B01L 9/52 414/752.1 |

* cited by examiner

SLIDE STORAGE, RETRIEVAL, TRANSFER, AND SCANNING SYSTEM FOR A SLIDE SCANNER

The current application claims a priority to the U.S. Provisional Patent application Ser. No. 62/378,812 filed on Aug. 24, 2016. The current application also claims a priority to the U.S. Provisional Patent application Ser. No. 62/378,814 filed on Aug. 24, 2016.

FIELD OF THE INVENTION

The present invention relates generally to digital pathology. More particularly, the present invention relates to a system for storage and retrieval of slides, and delivery of slides to a scanning stage for slide scanning.

BACKGROUND OF THE INVENTION

Microscopic examination of body fluids and tissue to determine the cause of disease has turned out to be the cornerstone of diagnosis in pathology. Traditionally, microscopic examination of body fluid samples or biopsy tissue mounted on glass slides has been performed by a pathologist using an optical microscope for the purpose of diagnosis. The Microscope slide would be loaded on such microscopes by hand for analysis and diagnosis. Due to passage of time, and required faster examination, automated microscopy gained momentum wherein the loading of the slides on such microscopes was automated to make the same more efficient. The stringent testing procedures and diagnostic requirements evolved in recent times required shorter processing times of the samples to address the plethora of samples to be tested. This triggered digital pathology. Digital pathology is the process of converting entire glass microscope slides into high resolution, whole-slide digital images that can be viewed, managed, analyzed and interpreted with a computer instead of a microscope using a digital pathology work flow management system.
This has given birth to digital whole slide scanners, which are used in the field of pathology to convert analog data on glass slides to digital images on computers for analysis.

Digital whole slide scanners available in the market use different mechanism for the purpose of holding and transporting slides through the scanner. Multiple options for automated digital scanners exists, a few of them are PL 200 by Prior Scientific, SF 210 by Nikon, SL 50 by GeniePix, Leica Biosystems, DMetrix, Ludl Electronics, Abbott Laboratories Inc., Pacard Instrument Company, to name a few. Such digital scanners have varying capacity ranging from processing one to hundreds of slides. A typically problem, however, is that scanners having small capacities cannot be scaled to meet the growing demands in terms of efficiency and volumes of the testing that can be handled by the scanner, whether in the digital scanner or otherwise. Various prior arts detailed as follows exists that disclose the ways of improving efficiency exists:

U.S. Pat. No. 6,847,481 discloses an automated slide loader. In accordance with the said disclosure of the patent, slide handler instrument is disclosed that transfers glass microscope slides from a cassette or magazine to a motorized microscope stage, having a slide exchange arm.

U.S. Pat. No. 6,905,300 describes a slide feeder with air bearing conveyor for use with a generic microscope. In accordance with the said disclosure of the patent, the stage is provided with a carriage moving horizontally along a direct path between the stage and the slide magazine.

U.S. Pat. No. 7,706,061 describes a method and apparatus for automating microscopic analysis of a plurality of data-encoded microscope slides. In accordance with the said disclosure of the patent, a slide engager is provided that engages the slide along the two lateral surfaces.

U.S. Patent Application No. 2008/0187464 describes an apparatus for feeding the microscope slides from a storage device to a slide stagy with the help of a sleeve. However there remains a need for a slide scaling mechanism to be used with slide scanners, which is robust, automated, accurate, simple to use, low cost and scalable. The present invention embodies one such concept.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention.

The present invention discloses a system for slide storage, retrieval, and transfer for slide scanning that is robust automated, accurate, simple to use, low cost and picks up slides of various thicknesses, holds them securely during the scanning process and deposits them back into slide storage once the scanning is complete.

Figure 1:
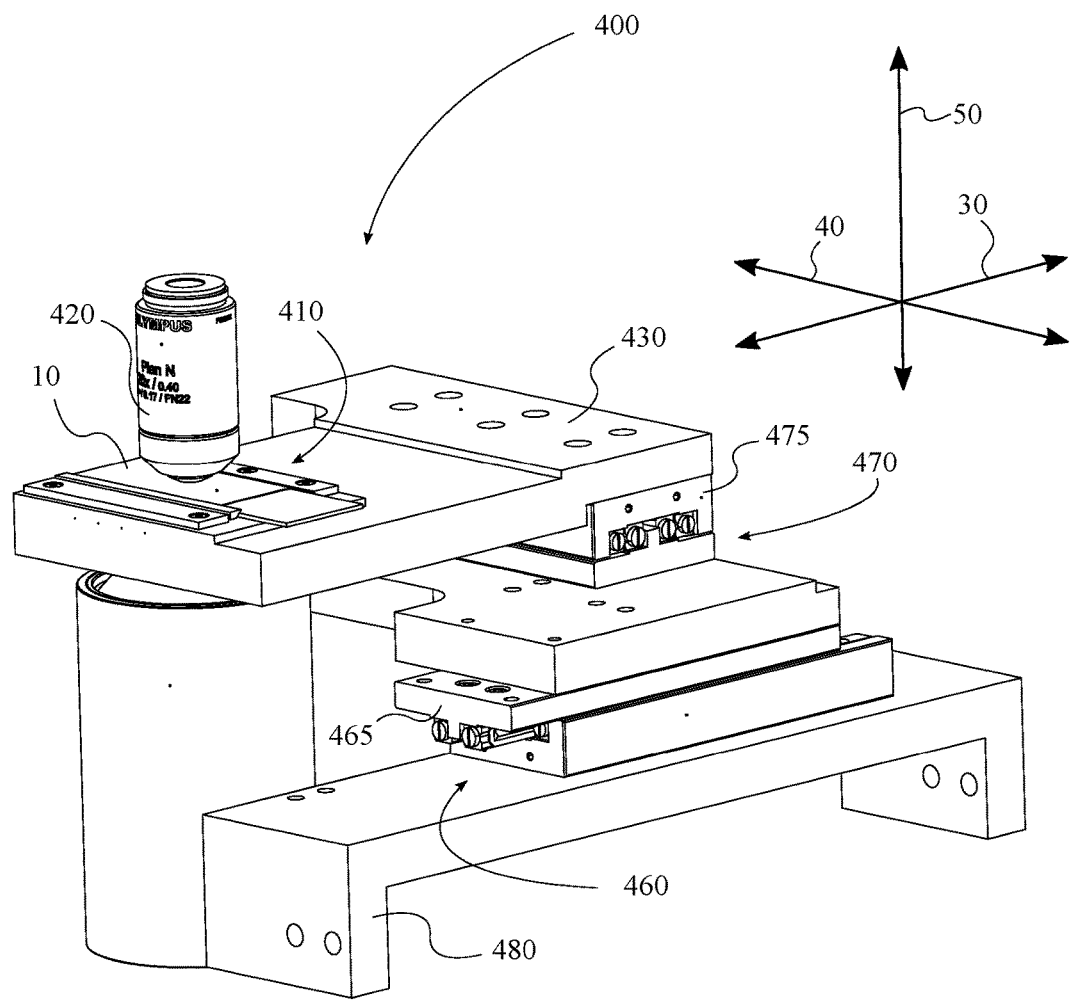
FIG. 1 is a perspective view of the slide scanning stage.

In general, the present invention comprises a slide scanning stage 400 as shown in FIG. 1 configured to receive a slide 10 into a slide holder 410 below a microscope objective 420, and further configured to move the slide holder 410 in relation to the microscope objective 420 in order to scan the slide 10.

Figure 2:
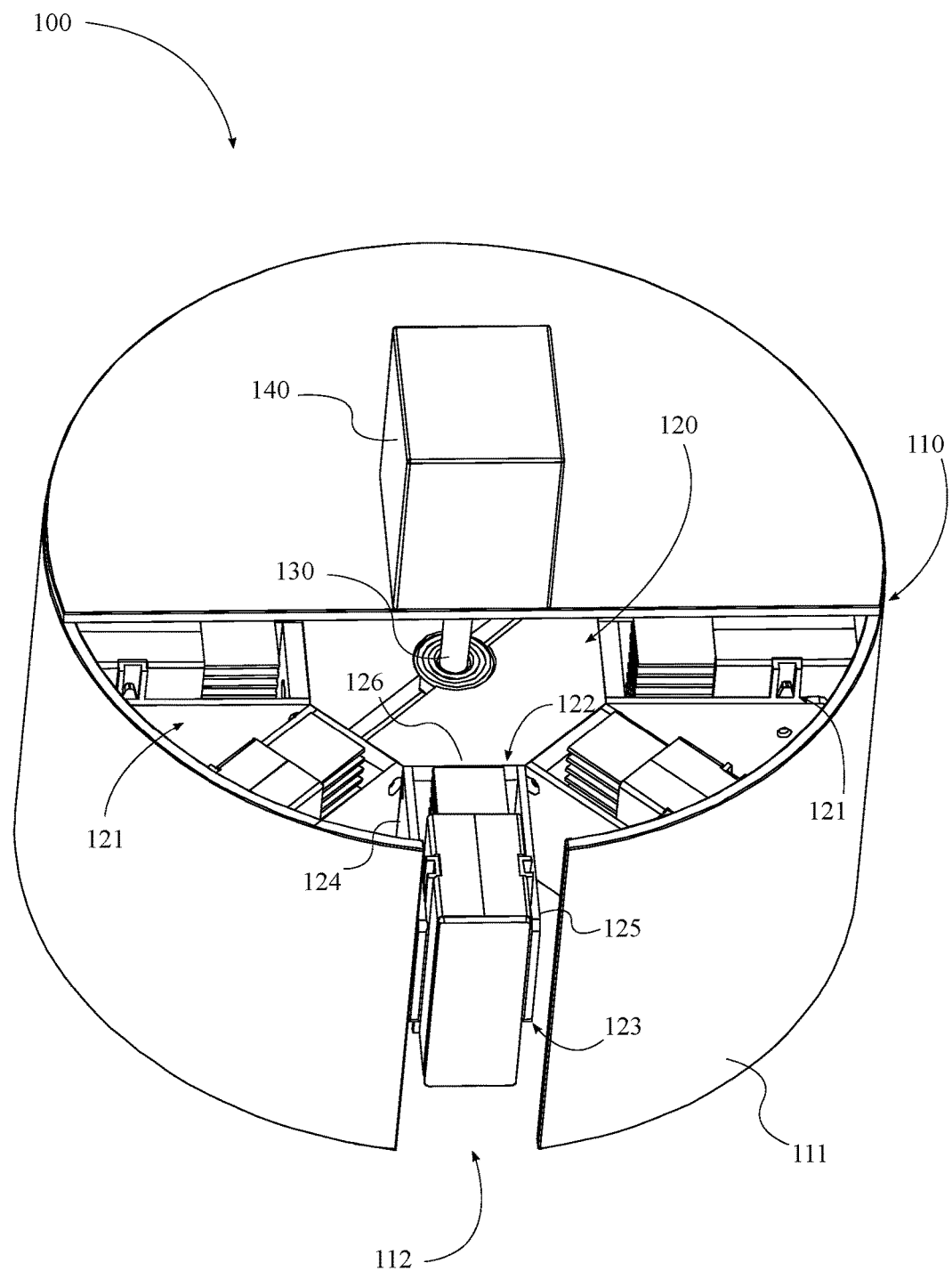
FIG. 2 is a perspective view of the slide storage assembly.

The present invention further generally comprises a slide storage assembly 100 as shown in FIG. 2 configured to store at least one slide basket 20, wherein each of the at least one slide basket 20 is configured to store a plurality of slides 10.

Figure 3:
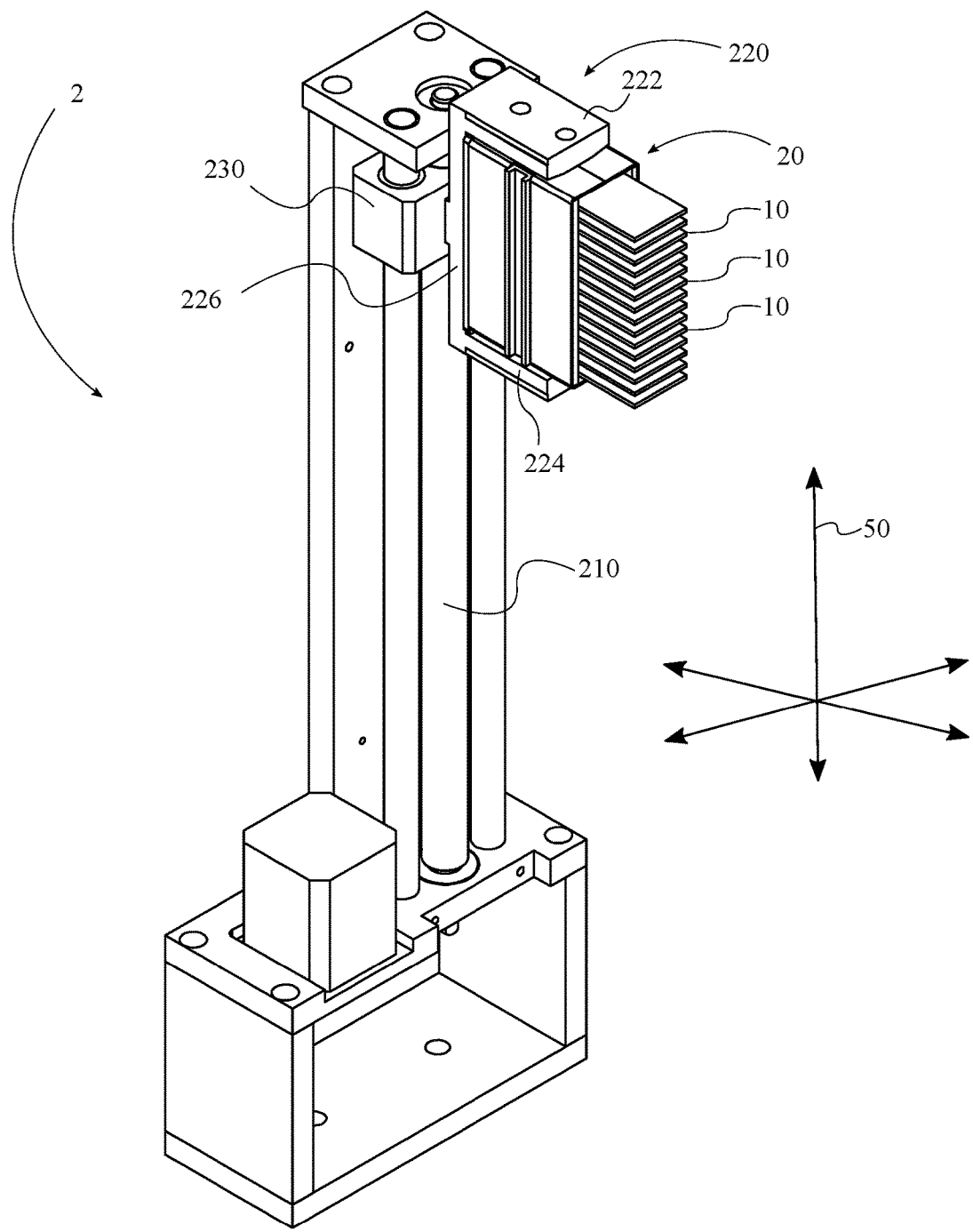
FIG. 3 is a perspective view of the slide basket transfer assembly.

The present invention further generally comprises a slide basket transfer assembly 200 as shown in FIG. 3 configured to retrieve and store the at least one slide basket 20 from and into the slide storage assembly 100, respectively.

Figure 4:
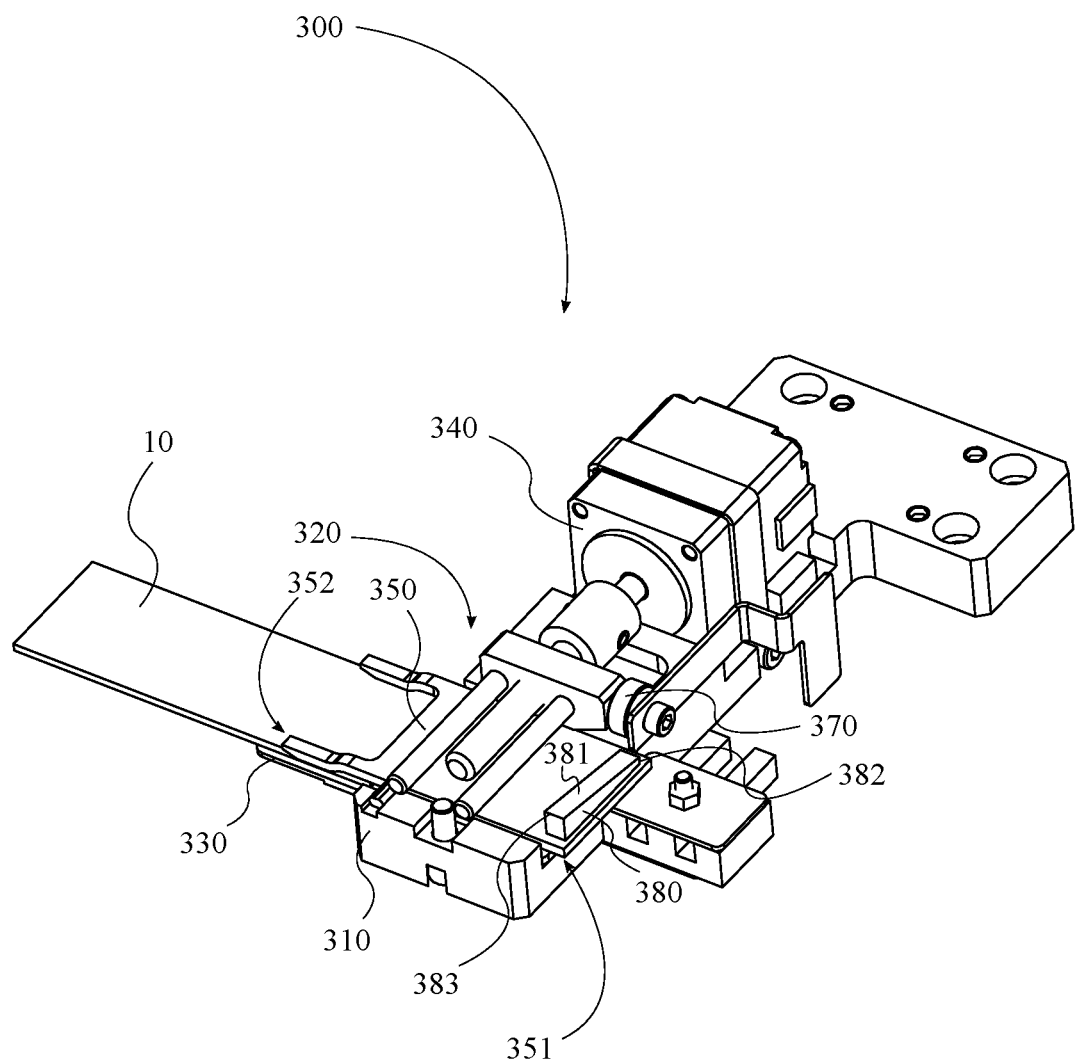
FIG. 4 is a perspective view of the slide transfer assembly.
Figure 6:
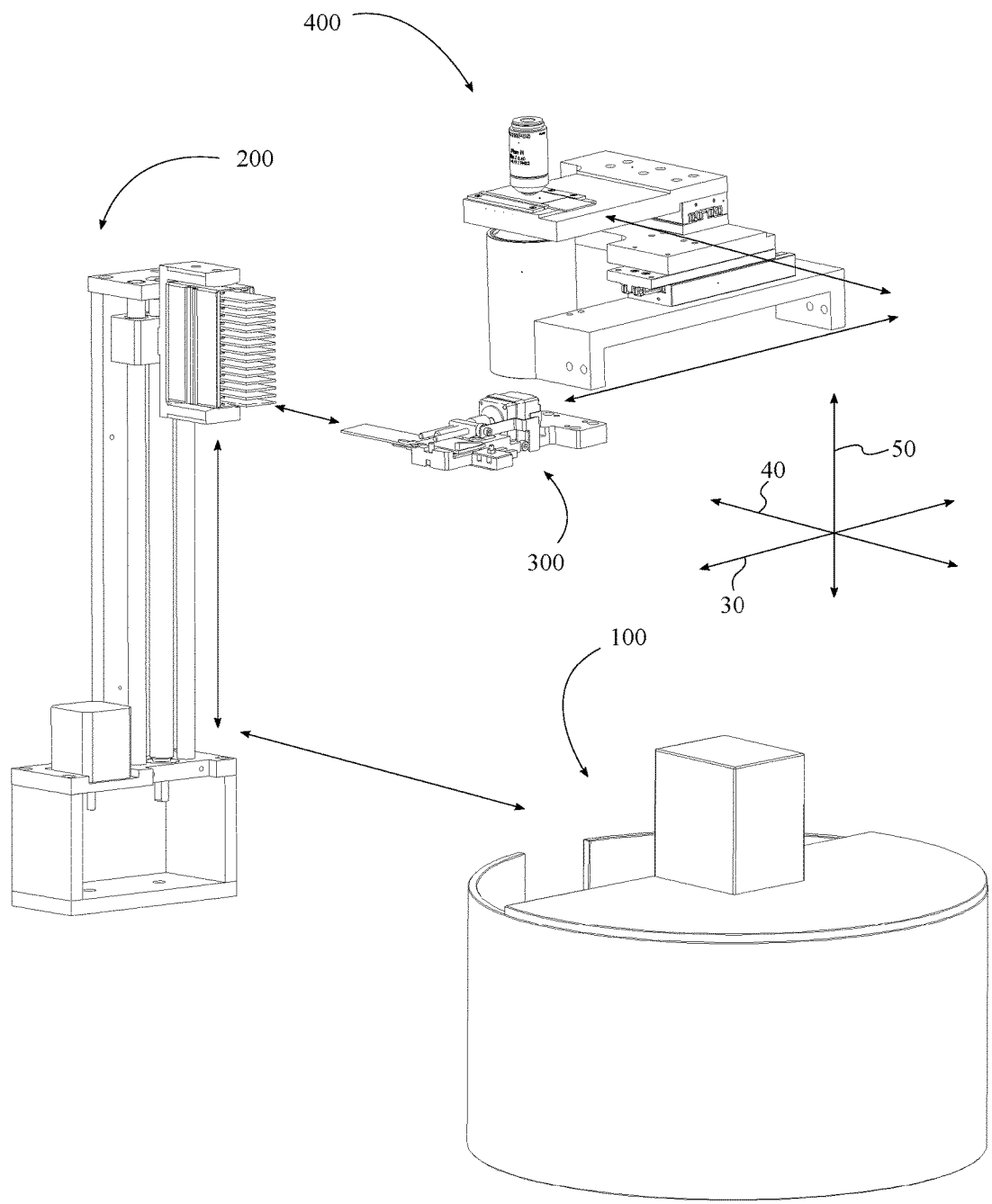
FIG. 6 is a general operational diagram for the system of the present invention.
Figure 7:
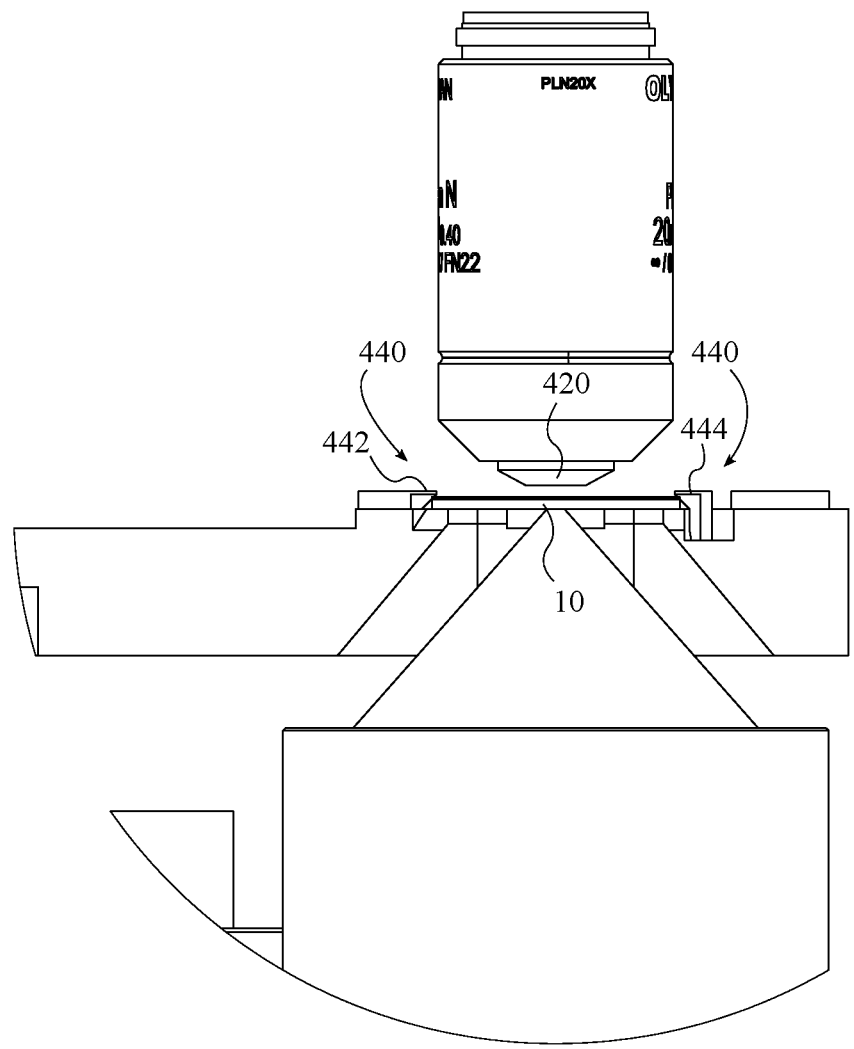
FIG. 7 is a side detail view of the slide holder of the slide scanning stage.

The present invention further generally comprises a slide transfer assembly 300 as shown in FIG. 4 configured to retrieve a slide 10 from the slide basket transfer assembly 200, deliver the slide 10 to the slide scanning stage 400 of a slide scanner, and return the slide 10 from the slide scanning stage 400 to the slide basket transfer assembly 200. From there, the slide basket transfer assembly 200 returns the slide basket 20 to the slide storage assembly 100. FIG. 6 shows an illustration of the general operation of the present invention in one embodiment.

The slide storage assembly 100 is a general storage area for slide baskets 20. Each slide basket 20 is configured to hold a plurality of slides 10. In some embodiments, each slide basket 20 can hold up to 15 slides 10 at a time, however this should not be considered to be limiting. The slide storage assembly 100 may contain slides 10 that need to be scanned and/or slides 10 that have already been scanned. It is contemplated that in some embodiments the present invention may comprise multiple instances of the slide storage assembly 100 for storage of different categories of slides 10.

Referring to FIG. 2, in some embodiments, the slide storage assembly 100 comprises a housing 110, a basket storage carousel 120, a shaft 130, and a motor 140. The basket storage carousel 120 is concentrically positioned within the housing 110. The basket storage carousel 120 comprises a plurality of basket storage slots 121. The plurality of basket storage slots 121 is radially positioned around the basket storage carousel 120. The shaft 130 is concentrically connected to the basket storage carousel 120, wherein the shaft 130 is surrounded by the plurality of basket storage slots 121. The motor 140 is operatively connected to the shaft 130 opposite the basket storage carousel 120, such that the motor 140 is operatively connected to the basket storage carousel 120 through the shaft 130 in order to rotate the basket storage carousel 120 within the housing 110. Each of the basket storage slots 121 being configured to removably receive one of the at least one slide basket 20. Furthermore, each of the at least one slide basket 20 may be removably attached within one of the basket storage slots 121.

In some embodiments, the housing 110 further comprises a lateral wall 111 and a basket transfer gap 112 traversing through the lateral wall 111, wherein the basket storage carousel 120 is configured through the motor 140 to radially position a specified basket storage slot from the plurality of basket storage slots 121 adjacent to the basket transfer gap 112, and wherein a slide basket 20 may be removed from or placed into one of the basket storage slots 121 through the basket transfer gap 112. In some embodiments, the housing 110 is not comprised.

In some embodiments, each of the plurality of basket storage slots 121 comprises a proximal end 122 and a distal end 123. The proximal end 122 is positioned adjacent the shaft 130, and the distal end 123 is positioned adjacent to the lateral wall 111 of the housing 110. Each of the basket storage slots 121 is configured to receive one of the at least one slide basket 20 through the distal end 123.

More particularly, in some embodiments, each of the plurality of basket storage slots 121 further comprises a first arm 124, a second arm 125, and a slot base 126. The slot base 126 is positioned at the distal end 123. The first arm 124 and the second arm 125 are connected perpendicular to the slot base 126, and the first arm 124 and the second arm 125 being separated from each other along the slot base 126, forming an open rectangular shape for holding a slide basket 20. The first arm 124 and the second arm 125 traverse from the slot base 126 to the distal end 123. In some embodiments, the slot base 126 is a singular, central component of the slide storage assembly 100 and concentrically connected around the shaft 130. Thus, in some embodiments each of the plurality of basket storage slots 121 is connected to the slot base 126.

Referring to FIG. 3, in some embodiments, the slide basket transfer assembly 200 comprises a track 210 and a slide basket holder 220. The slide basket holder 220 is configured to move along the track 210, and the slide basket holder 220 being configured to removably receive a slide basket 20. In some embodiments, the slide basket holder 220 is configured to traverse in a vertical direction along the track 210. More specifically, the slide basket holder 220 of the slide basket transfer assembly 200 may be configured to move vertically along a Z axis 50 in order to transfer a slide basket 20 from the slide storage assembly 100 to the slide transfer assembly 300. However, the direction the slide basket holder 220 traverses should not necessarily be limited to the vertical direction, and different configurations of the present invention may comprise different arrangements in terms of the direction of travel of the slide basket holder 220. The primary requirement for the slide basket holder 220 is to traverse between a location appropriate for retrieval of a slide basket 20 from the slide storage assembly 100, and a location appropriate for the slide transfer assembly 300 to retrieve individual slides from the slide transfer basket.

In some embodiments, the slide basket transfer assembly 200 further comprises a track engagement portion 230, and furthermore the slide basket holder 220 comprises an upper basket holder arm 222, a lower basket holder arm 224, and a connecting arm 226. The track engagement portion 230 is moveably engaged along the track 210. The track 210 and track engagement portion 230 may be connected together in any appropriate manner that allows the track engagement portion 230 to move along the track 210. For example, in some embodiments, the track 210 may comprise a lead screw driven by a stepper motor engaged with the track engagement portion 230. As the motor turns the lead screw, external threading of the lead screw engaged with internal threading of the track engagement portion 230 to move the track engagement portion 230 along the track 210.

In some embodiments, the slide basket holder 220 is connected to the track engagement portion 230 opposite the track 210. The lower basket holder arm 224 is terminally and perpendicularly connected to the connecting arm 226, while the upper basket holder arm 222 is terminally and perpendicularly connected to the connecting arm 226 opposite the lower basket holder arm 224, forming an open rectangle for holding a slide basket 20 in a similar manner to the basket storage slots 121 of the slide storage assembly 100. The slide basket holder 220 is thus configured to removably receive a slide basket 20 between the upper basket holder arm 222 and the lower basket holder arm 224.

The slide transfer assembly 300 functions to retrieve an individual slide 10 from the slide basket transfer assembly 200 and transfer the slide 10 to the slide scanning stage 400 for scanning. It is contemplated that in various embodiments, the slide transfer assembly 300 may take many forms depending on a variety of factors, such as, but not limited to, machining tolerances, design requirements, engineering practicalities, cost, of other real-world application considerations. However, in essence, the basic requirements of the slide transfer assembly 300 are to be able to move in space in order to grasp an individual slide 10 from the slide basket transfer assembly 200, remove the slide 10, move the slide 10 to the slide scanning stage 400, and place the slide 10 into an appropriate position for scanning on the slide scanning stage 400.

Figure 5:
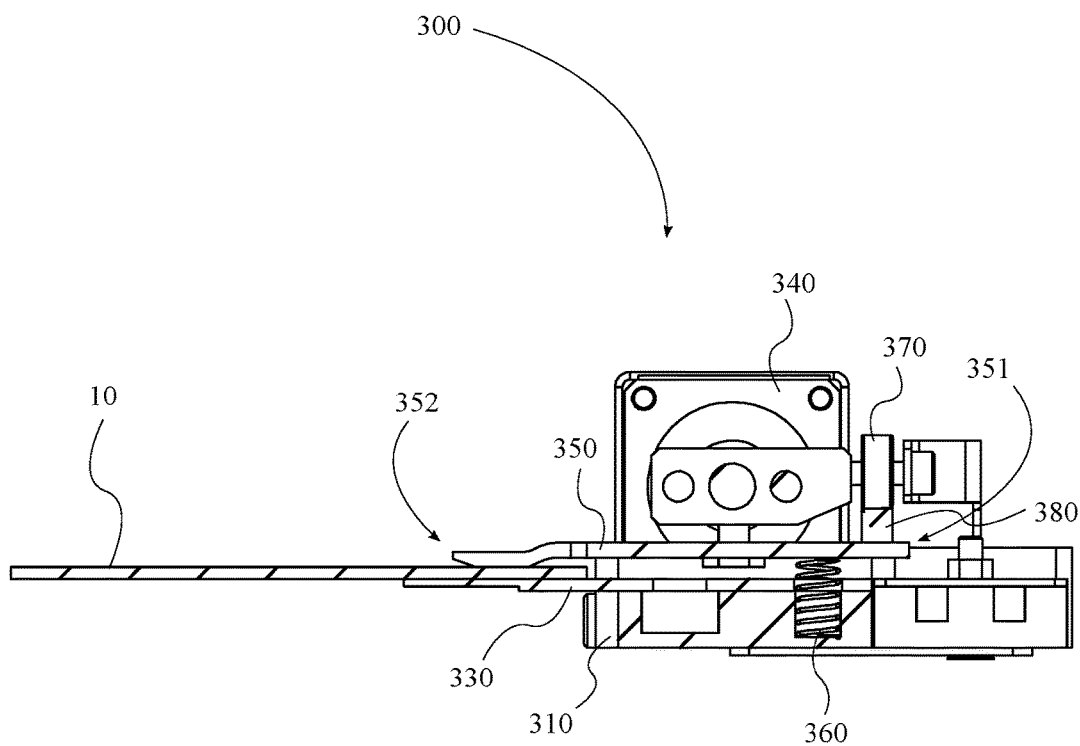
FIG. 5 is a side sectional view of the slide transfer assembly.
Figure 5:
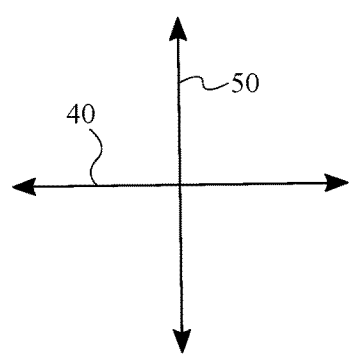

Referring to FIGS. 4-5, in general, in some embodiments, the slide transfer assembly 300 may comprise a support base 310, a slide grasping mechanism 320, and a slide support 330. The slide support 330 is positioned on the support base 310, and should be understood to be the location on the slide transfer assembly 300 a slide 10 is secured into for transfer. The slide support 330 may comprise a groove, a platform, a flat surface, or any other desired or applicable form factor.

The slide grasping mechanism 320 is integrated onto the support base 310 around the slide support 330, wherein the slide grasping mechanism 320 is configured to retain a slide 10 on the slide support 330. It is contemplated that many means of securing a slide 10 onto the slide support 330 may be utilized. However, one exemplary embodiment of the slide grasping mechanism 320 is herein disclosed.

In some embodiments, the slide transfer assembly 300 further comprises a motor 340, a lip arm 350, a fulcrum 360, a ramp roller 370, and a ramp block 380. The lip arm 350 is positioned atop the slide support 330. The lip arm 350 is a component of the current exemplary embodiment that applies force to the slide 10 to secure the slide 10 in place on the slide support 330. The lip arm 350 comprises a proximal lip arm end 351 and a distal lip arm end 352. The distal lip arm end 352 of the lip arm 350 applies force to the slide 10 in order to grasp the slide 10.

In the current exemplary embodiment, the slide grasping mechanism 320 employs a lever mechanism to grasp and release the slide 10. Thus, the lip arm 350 is positioned atop the fulcrum 360, with the fulcrum 360 being positioned between the proximal lip arm end 351 and the distal lip arm end 352. In some embodiments, the fulcrum 360 is a spring. Thus, while no force is applied to the proximal lip arm end 351, the distal lip arm end 352 is forced downward onto the slide 10 or slide support 330.

The ramp block 380 is connected atop the proximal lip arm end 351. The motor 340 is operatively engaged with the ramp roller 370 such that the motor 340 is configured to linearly advance the ramp roller 370 up the ramp block 380 in order to raise the distal lip arm end 352 away from the slide support 330. In some embodiments, the ramp block 380 may resemble a right triangle. In any case, the ramp block 380 should comprise a sloped edge 381, such that a lower end 382 of the sloped edge 381 is positioned between the ramp roller 370 and an upper end 383 of the sloped edge 381. Thus, as the ramp roller 370 is constrained to move in a linear path towards the ramp block 380, as the ramp roller 370 comes into contact with the lower end 382 of the ramp block 380 and moves toward the upper end 383 of the ramp block 380, downward force is progressively applied to the ramp block 380 and thus the proximal lip arm end 351 of the lip arm 350, thus lifting the distal end 123 lip arm 350 of the lip arm 350 and allowing a slide 10 to be either inserted or removed from the slide support 330.

In another embodiment, the ramp block 380 is not pressed down by linear motion of a ramp roller 370 onto the ramp block 380. Rather, the motor 340 is rotatably engaged with a cam, such that the cam can be rotated by the motor 340 to appropriate positions in order to apply and release force on the ramp block 380 in order to open or close the lip arm 350. Moreover, it is further contemplated that other variations of means for opening and closing the lip arm 350 and even more generally, for grasping and releasing a slide 10, may be comprised in alternative embodiments herein not disclosed.

As previously noted, the primary function of the slide transfer assembly 300 is to transfer a single slide 10 from the slide basket transfer assembly 200 to the slide scanning stage 400. It is hereby contemplated that in various embodiments, various configurations of the present invention may be utilized to accomplish this purpose. For example, in some embodiments, the support base 310 of the slide transfer assembly 300 is configured to move horizontally in an X-Y plane in order to transfer a slide 10 from the slide basket transfer assembly 200 to the slide scanning stage 400 of the slide scanner, wherein the X-Y plane is perpendicular to the Z axis 50. However, this should not be considered a limiting arrangement, and in other embodiments, the slide transfer assembly 300 may be configured to move in three dimensions in order to transfer a slide 10. Any applicable and desirable means may be utilized in order to facilitate movement of the slide transfer assembly 300 through space, such as, but not limited to, a plurality of linear track 210s coupled with respective motors along which the slide transfer assembly 300 traverses, or a robotic arm that is capable of translating and even potentially rotating the slide transfer assembly 300 in three-dimensional space, or the like.

Further disclosed herein is an arrangement for a slide scanning stage 400. The slide scanning stage 400 is a platform upon which a slide 10 is placed for scanning through a microscope objective 420.

Referring to FIGS. 1 and 7-9, in some embodiments, the slide scanning stage 400 comprises a slide holder stage 430, a slide securing mechanism 440, a slide insertion and ejection mechanism 450, an X axis movement mechanism 460, and a Y axis movement mechanism 470. The slide holder stage 430 is a structural component used for supporting the slide holder 410, thus, the slide holder 410 is positioned on the slide holder stage 430. The slide holder 410 may be understood to be the location the slide 10 is placed for scanning. The slide securing mechanism 440 is integrated around the slide holder 410, wherein the slide securing mechanism 440 secures a slide 10 within the slide holder 410 for scanning so that the slide 10 does not move. The slide insertion and ejection mechanism 450 are integrated around the slide holder 410, wherein the slide insertion and ejection mechanism 450 is configured to alternatingly insert the slide 10 into the slide holder 410 and eject the slide 10 from the slide holder 410. It is contemplated that in various embodiments the slide holder 410 may have a variety of configurations that produce the end result of holding a slide 10 securely in place, and the aforementioned arrangement should not be considered to be limiting.

When the slide transfer assembly 300 delivers the slide 10 to the slide scanning stage 400, the slide transfer assembly 300 may only deliver the slide 10 partway into the slide holder 410. Thus, the slide 10 insertion end ejection mechanism must push the slide 10 fully into the slide holder 410. Conversely, the slide transfer assembly 300 requires at least a portion of the slide 10 to be exposed in order to grasp the slide 10. Thus, the slide insertion and ejection mechanism 450 pushes the slide 10 partially out of the slide holder 410 for transfer back to the slide basket transfer assembly 200 by the slide transfer assembly 300.

The slide holder stage 430 is operatively connected to the X axis movement mechanism 460 and the Y axis movement mechanism 470, wherein the X axis movement mechanism 460 and the Y axis movement mechanism 470 are jointly configured to move the slide holder stage 430 in an X-Y plane beneath the microscope objective 420.

Figure 8:
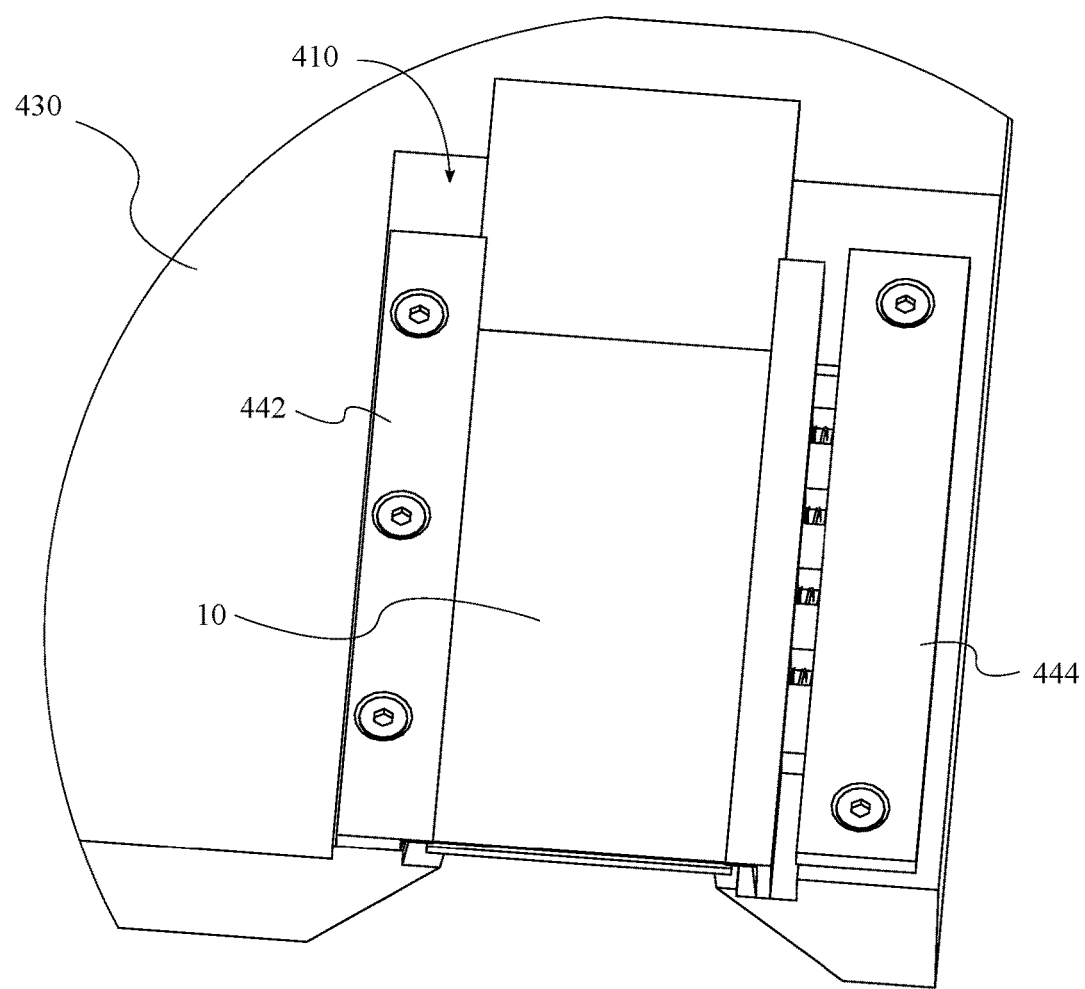
FIG. 8 is a perspective detail view of the slide holder.
Figure 9:
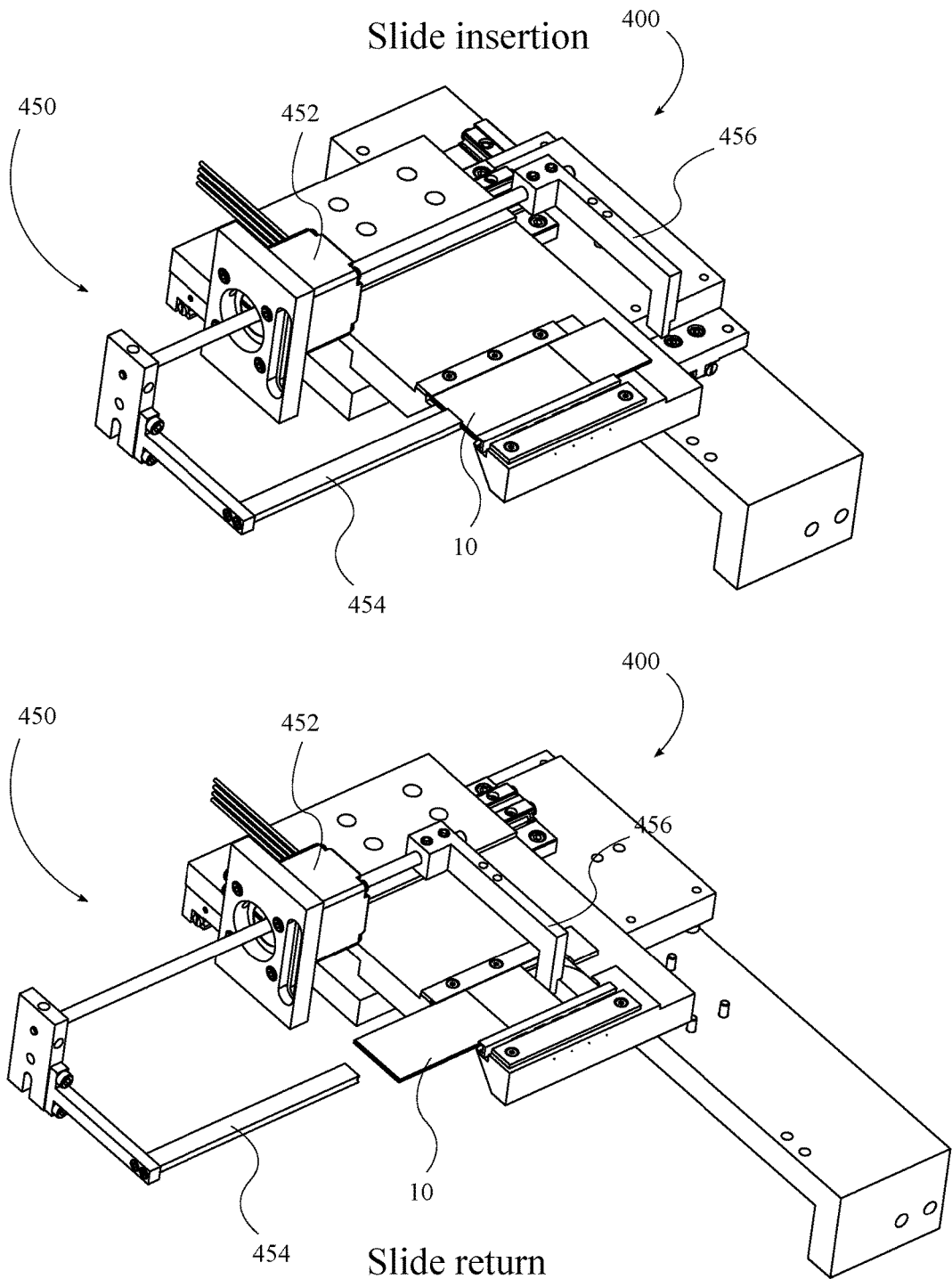
FIG. 9 is a perspective illustration of the operation of the slide insertion and ejection mechanism of the slide scanning stage.

More particularly, in some embodiments the slide securing mechanism 440 comprises a fixed slide holder 442 and a movable slide holder 444. The fixed slide holder 442 and the movable slide holder 444 are laterally opposite each other along the slide holder 410, wherein the slide 10 is held in place by the fixed slide holder 442 and the movable slide holder 444. The slide 10 is inserted into the slide holder 410 between the fixed slide holder 442 and the movable slide holder 444. In some embodiments, the movable slide holder 444 being spring-loaded, as can be seen in FIG. 8, such that compression is applied to the slide 10 by the movable slide holder 444 while the slide 10 is positioned within the slide holder 410.

In some embodiments, the slide insertion and ejection mechanism 450 comprises a slide actuation motor 452, a slide insertion arm 454, and a slide 10 return arm. In some embodiments, the slide actuation motor 452 is operatively engaged with the slide insertion arm 454 and the slide 10 return arm, such that the slide insertion arm 454 and the slide 10 return arm move linearly and synchronously with each other through the slide actuation motor 452. Furthermore, the slide insertion arm 454 and the slide ejection arm 456 being positioned opposite each other across the slide holder 410, such that the slide insertion arm 454 presses against the slide 10 in order to insert the slide 10 into the slide holder 410 upon actuation of the slide actuation motor 452 in an insertion direction, and such that the slide ejection arm 456 presses against the slide 10 in order to eject the slide 10 from the slide holder 410 upon actuation of the slide actuation motor 452 in an ejection direction, wherein the ejection direction is the reverse of the insertion direction.

Moreover, the slide scanning stage 400 may further comprise an X axis movement stage 465 as the X axis movement mechanism 460, and a Y axis movement stage 475 as the Y axis movement mechanism 470. The X axis movement stage 465 and the Y axis movement stage 475 may in some embodiments be understood to be structural, generally flat components, where "stage" herein refers to a structural body.

In some embodiments, the X axis movement stage 465 is connected to a stage base 480, wherein the X axis movement stage 465 is configured to move along an X axis 30 atop the stage base 480. Moreover, the Y axis movement stage 475 is connected atop the X axis movement stage 465, wherein the Y axis movement stage 475 is configured to move along a Y axis 40 atop the X axis movement stage 465. Finally, the slide holder stage 430 is connected atop the Y axis movement stage 475. Thus, through combination of movement of the X axis movement stage 465 and the Y axis movement stage 475, the slide holder stage 430 is able to be moved to any point in the X-Y plane. Thus, the slide 10 may be moved beneath the microscope objective 420 in order to capture many images of small regions of the slide 10 which can then be digitally stitched together.

The following is an alternative, exemplary disclosure of several aspects of the present invention (in particular, the slide basket transfer assembly 200 and the slide storage assembly 100), is intended to further demonstrate the spirit of the present invention, and should not be considered to be limiting.

The slide basket transfer assembly 200 comprises means for feeding the slides 10 to the slide transfer assembly 300. In accordance with the preferred embodiment of the present invention a slide basket holder 220 is provided that engages the slide basket 20 with slides 10 stacked in it. The slide basket 20 is a detachable, rectangular metal frame, with slots to hold slides 10. The slides 10 are manually placed into the slide basket 20 that is latched into the slide basket holder 220. In accordance with the present invention, a typical slide basket 20 has slots, but this should not be seen as a limitation of the present invention. The slide basket transfer assembly 200 further comprises a vertical rod that enables movement of the slide basket holder 220 in a vertical manner along the rod at the Z axis 50. This is essential for the purposes of the present invention to enable the slide transfer assembly 300 to pick the next slide 10 in the imaging process. This movement of the slide basket holder 220 can preferably be enabled with the aid of a stepper motor based linear translational stage provided that support linear motion. In accordance with the preferred embodiment of the present invention, the slide basket holder 220 functions and moves along the rod at the instructions of a computer command. This is, however, not a limitation of the present invention as the movement of the slide basket holder 220 can be automated and operational in any other desired manner.

In accordance with the preferred embodiment of the present invention, the slide basket holder 220 has prefixed latching means, in such numbers as may be desired, that engage the slide basket 20 with the slide basket holder 220. In accordance with the further preferred embodiment of the present invention, the latching means are spring loaded screws and six of them are provided in accordance with the present invention.

In accordance with the present invention, the slide basket holder 220 travels to a predefined position, in a manner that it aligns in one plane with the slide 10 grabbing mechanism or the slide storage assembly 100, as the case may be.

The slide storage assembly 100 in accordance with the present invention is a detachable plug and play slide storage assembly 100. This, however, should not be seen as a limitation of the present invention, and the slide storage assembly 100 disclosed in accordance with the present invention can be made an integral part of the scanner.

In accordance with the present invention, as illustrated in Fig., the slide storage assembly 100 provides slides 10 to the slide basket transfer assembly 200 of a scanner. The slide storage assembly 100 comprises a basket storage carousel 120 with one or more pair of arms such that each pair of arm is capable of holding a slide basket 20; a center shaft 130 that aids in rotating the basket storage carousel 120 along with the pair of arms; a motor 140, and housing 110 means to house the slide storage assembly 100, in such a manner that the slide basket 20 can be engaged and disengaged in the slide basket holder 220 at a predefined position.

In accordance with the present invention, the basket storage carousel 120 comprises one or more pair of arms such that each pair of arm is capable of holding slide basket 20 and can be rotated. In accordance with the preferred embodiment of the present invention, eight pairs of arms are deployed which in turn has a capacity to feed and process slides 10. This, however, should not be considered a limitation of the present invention and it is apparent to the person skilled in the art that such pairs of arms can be added as may be desired for scalability. In accordance with the present invention the pair of arms are attached to the other pair of arms by any attaching means as may be known in the industry, in a manner that can facilitate rotating the basket storage carousel 120 along with the pair of arms and engage and or disengage the slide basket 20 with/from the slide basket holder 220 at the predefined position. In accordance with the preferred embodiment of the present invention, the eight pairs of arms are attached to each other in a circular pattern so as to look like a wheel. Alternatively, the one or more pair of arms can be attached directly to the center shaft 130 independently or individually by the help of attaching means as may be suitable to the deployer.

In accordance with the embodiment of the present invention, the slide storage assembly 100 further comprises a center shaft 130 and is placed at the center of the basket storage carousel 120 with one or more pair of arms. In accordance with an aspect of the present invention, the basket storage carousel 120 with one or more pair of arms is attached to the center shaft 130 directly or is attached to each other as has been stated above. In accordance with an aspect of the present invention, the basket storage carousel 120 with one or more pair of arms is attached to the center shaft 130 at a place convenient to the deployer and in such a manner that the slide storage assembly 100 is workable, with attaching means as may be known in the industry such as, but not limited to, screws, pins, and the like. In accordance with the further embodiment of the present invention, one end of the center shaft 130 is attached to a motor 140 that provides sufficient rotator function to the entire assembly so that the slide basket 20 can be engaged and or disengaged from the slide basket holder 220, when the slide basket holder 220 is aligned within the pair of the arms so as to place the slide basket 20 between the pair of arms, where the said processed slide basket 20 would be disengaged and on rotation, the next pair of arm having a fresh slide basket 20 to be processed is engaged in the slide basket holder 220. The movement of the basket storage carousel 120 and the one or more pair of arms can preferably be enabled with the aid of a stepper motor 140 provided for a rotator motion. In accordance with the preferred embodiment of the present invention, the slide storage assembly 100 functions and the basket storage carousel 120 with one or more pair of arms function and move at the instructions of a computer command. This is, however, not a limitation of the present invention as the movement of the slide storage assembly 100 and the basket storage carousel 120 can be automated and operational in any other desired manner. As has been stated above, the movement of the basket storage carousel 120 and the one or more pair of arms can preferably be enabled with the aid of a stepper motor 140 provided for a rotator motion. However, it is apparent to a person skilled in the art that the present invention can be deployed in linear motion with necessary adaptations.

In accordance with the further embodiment of the present invention, the slide storage assembly 100 further comprises housing 110 means to house the slide storage assembly 100. In accordance with the preferred embodiment of the present invention, the slide storage assembly 100 is housed in the housing 110 means such that the slide basket holder 220 travels to the top of the bar in such a manner that the slide basket holder 220 aligns into the cavity in such a manner that the slide basket 20 faces inside the housing 110 means, and the slide basket 20 in between the pair of arm and is latched with the latching means of the pair of the arm. In accordance with the preferred embodiment of the present invention, the latching means disengages the slide basket 20 from the slide basket holder 220 and when the basket storage carousel 120 rotates on supply from electrical source, the pair of arm in which the slide basket 20 is now engaged is removed from the slide basket holder 220. When the basket storage carousel 120 rotates, the next pair of arm that carries afresh slide basket 20 is engaged in the slide basket holder 220, which is then carried by the slide basket transfer assembly 200 for further processing and imaging.

In accordance with an aspect of the present invention, the above said process is repeated for all the eight pair of arms, and thus, depending upon the load, the scanning can be scaled as per required. As has been stated above, the scaling can be increased by increasing the pair of arms disclosed in accordance with the present invention.

The following is a further alternative, exemplary disclosure of several aspects of the present invention (in particular, the slide transfer assembly 300), is intended to further demonstrate the spirit of the present invention, and should not be considered to be limiting.

In accordance with the present invention, the slide basket transfer assembly 200 travels to a predefined position, in a manner that the slide basket 20 aligns the desired slide 10 in one plane with the lips of a slide 10 grabbing mechanism provided and described herein.

The slides 10 are provided for the slide transfer assembly 300 by the slide 10 feeder assembly. The slide transfer assembly 300 comprises a metallic plate that holds the slide 10; the lip arm 350 assembly which is responsible for holding the slide 10 against the metallic plate, thus enabling the thickest of the slides 10 to be engaged. The slide 10 is sandwiched between the lip arm 350 assembly and the metallic plate, ensuring safe positioning of the slide 10 and avoiding falls or breakage.

In accordance with the embodiment of the present invention, the lip arm 350 assembly is controlled by a stepper motor 340 assembly which sits on the metallic plate, adjacent to the lip arm 350 assembly. The stepper motor 340 assembly is fixed to the metallic plate by fixing means that provide sufficient play to the motor 340 to control the rotation of the lip arm 350 assembly. The fixing means in accordance with the present invention can be any known means such as screws, pivot pin, and like, but not limited.

In accordance with further embodiment of the present invention, the slide 10r grabber mechanism comprises springs, which are sandwiched between the rear end of the stepper motor 340 assembly and the metallic plate. These springs load the lip arm 350 assembly on the slide 10 and create the force required for holding the slide 10 securely.

In accordance with the further embodiment of the present invention, the back of the lip assembly is connected to a ramp roller 370 which moves along a ramp, in order to open and close the lip. Opening and closing of the lip arm 350 assembly is controlled by the stepper motor 340, in a manner in which, the activation of the stepper motor 340 moves the ramp roller 370 up the ramp, thereby compressing the springs which open the lip arm 350. These components constitute the ramp actuating mechanism, which lies on to the metallic plate.

In further accordance with the embodiment of the present invention, the slide 10 grabbing mechanism comprises a slide 10 detect sensor which is a mechanical switch, but not limited to such, and is fixed to the back of metallic plate. This sensor performs two important functions namely: detect the presence or absence of a slide 10, and, detect dispositioning of the slide 10, or detect the collision of slide 10 with a foreign object. The switch is activated once it comes in contact with the slide 10, thus signaling incorrect motion/activity of the slide 10.

In accordance with the embodiment of the present invention, the lip arm 350 assembly is provided with cushioning made of friction creating material, not limited to rubber/plastic, in order to provide better friction and stronger grip.

In accordance with one embodiment of the present invention, the slide transfer assembly 300 is provided with a holder means that enables the movement of the slide transfer assembly 300 assembly in a horizontal plane to reach the slide basket 20 to pick the desired slide 10. In accordance with the preferred embodiment of the present invention, the slide transfer assembly 300 mechanism moves along Y axis 40 to reach the slide basket 20 to pick the desired slide 10, however, this should not be considered as a limitation of the present invention. This is essential for the purposes of the present invention to enable the slide transfer assembly 300 to pick the next slide 10 in the imaging process. The slide transfer assembly 300 is attached to the holder means with the aid of any attaching means including, but not limited to, screws, welding, pivot pin, and like. The movement of the slide transfer assembly 300 can preferably be enabled with the aid of stepper motor 340 based linear translational stages provided. In accordance with the preferred embodiment of the present invention, the movement of the slide transfer assembly 300 is controlled at the instructions of a computer command. This is, however, not a limitation of the present invention as the movements of the slide transfer assembly 300 can be automated and operational in any other desired manner. In accordance with the embodiment of the present invention, once the slide 10 is picked by the slide transfer assembly 300, the slide transfer assembly 300 acts as a stage and takes the slide 10 under the microscope's objective lens for digital imaging. In accordance with the preferred embodiment of the present invention, the slide transfer assembly 300 moves at X axis 30 with the aid of another stepper motor 340 based linear translational stage provided to take the slide 10 under the microscope's objective lens for digital imaging. In accordance with the preferred embodiment of the present invention, such movements of the slide transfer assembly 300 are controlled at the instructions of a computer command.

In accordance with the embodiment of the present invention, once the slide 10 (to be picked) is moved to a specific location (aligned in such a manner to enable the slide transfer assembly 300 to pick the slide 10), the slide transfer assembly 300 is moved towards the slide basket 20, so that the slide 10 is now within its top and bottom plate (the lips). The stepper motor 340 assembly activates the ramp roller 370, enabling it to move down the ramp, thus closing the lip arm 350.

Once the scanning is complete, the slide 10 is moved back to its original position against the basket by the X-Y stage. Once the slide 10 is aligned against the desired slot of the basket, the stepper motor 340 activates the ramp roller 370, allowing the roller to move up the ramp, thus opening the lip arm 350 and releasing/depositing the slide 10.

The following is a further alternative, exemplary disclosure of several aspects of the present invention (in particular, the slide 10 stage assembly), is intended to further demonstrate the spirit of the present invention, and should not be considered to be limiting.

Digital pathology scanners have challenging requirements for scanning and producing digital images of pathology specimen slides 10. Images require high magnification and resolution for adequate diagnosis of the patient. Most systems typically use microscope objectives up to 60× magnification. Consequently, these objectives typically have working distance of <1.0 mm, depth of focus <+/−1.0 um and field of view <250 um, which could require thousands of images stitched together to cover a specimen on a standard microscope slide 10 of 75 mm×25 mm×1 mm. Additionally, these types of objectives require high numerical aperture (NA) illumination light. These types of light sources called "Condensers" typically have <10 mm working distance, located on the opposing side of the specimen slide 10 from the objective (transmitted light).

Digital pathology instruments have design challenges to scan specimen slides 10 with these optical constraints. The scan stage must securely hold a specimen slide 10 and move the slide 10 under the optical system to maintain flatness to within the objective's depth of focus to produce high resolution images (e.g., image in focus). The stage must also hold the specimen slide 10 in a manner to not obstruct either the objective or the condenser.

Typical design considerations when producing a specimen scanning stage include:
1. Linear rails to move the entire scan area of the slide 10 in X & Y with run-out (non-linearity of motion)<depth of focus.
2. Drive systems to move the rails without inducing additional run-out.
3. Methods to securely hold the slide 10 and ability to insert and return the slide 10 from the stage.
4. Maintain slide 10 perpendicularity to optical system for all slides 10 scanned.

The following design embodiments address the above concerns:
1. General stage design to meet specifications described above including flatness of motion and ability to not obstruct the optical system.
2. "Flexure" design to reduce/eliminate drive system induced run-out.
3. Slide securing mechanism 440 on stage.
4. Method to insert and return slide 10 from stage.
5. Manufacturable method to hold multiple slides 10 perpendicular to optical system.

The general stage design in some embodiments consists of two precision cross roller tables (in this embodiment) with sufficient travel to scan a specimen slide 10 in X & Y directions. The stages are offset from the slide 10 to allow clearance for the objective above and condenser below. Cross roller stages were selected to provide minimal run-out, rigidity to sustain motion performance when offset from optical system and enough travel to support slide 10 handling and scanning.

Some embodiments implement a flexure drive system. In some embodiments, the stages are driven by a stepper motor with an integrated leadscrew (Haydon-Kerk). The motor assembly includes an anti-backlash nut and combined with small pitch leadscrew and micro-stepping, very small and repeatable motions are possible. A detriment of this design is, when directly connected to a stage, stepper motor induced vibration and wobble of the leadscrew create excessive run-out to the stage. To avoid, a flexure is inserted between the drive system and the stage. In this case a steel wire is used (approximately 0.025 inch diameter). A steel wire allows axial push and pull, but bends to resist all non-axial induced motion. The wire is attached to the leadscrew's anti-backlash nut and the stage as shown below. The stepper motor drives the leadscrew back and forth which pulls the stage on the linear rails without increasing run-out.

The specimen slide 10 requires secure mounting on the stage so as to not obstruct the optical system (Objective & Condenser). Additionally, the slide 10 must be perpendicular to the optical system or parts of a single field of view (FOV) will appear out of focus. The slide holder 410 shown below consists of a fixed holder side and a movable holder side. The movable holder is spring loaded and expands to accept the slide 10 during insertion onto stage. Chamfers are on both holders forcing the slide 10 down against the stage which acts as the scanning reference plane. The down force is maintained by spring force and accommodates different slide 10 widths. In this embodiment, horizontal and vertical chamfers are added to the entrance of the stage so any misalignment during slide 10 insertion onto the stage is supported. It should be noted that high NA condensers require stage clearance to allow uniform illumination of the slide 10 even while scanning the edge of the slide 10. Moreover, the ends of the slide 10 are exposed to support slide 10 handling on and off the stage.

Reliable slide 10 insertion and return from the stage is essential for Digital Pathology. Specimen collection and preparation is costly and uncomfortable for the patient. Consequently, a broken slide 10 due to mishandling should be avoided. In this embodiment, a single motor with non-captive leadscrew (Haydon-Kerk) has a slide 10 insertion and return arm connected to either end of the leadscrew. Actuation of the motor causes the leadscrew to move through the motor and move the arms in the desired direction. The insertion arm accommodates a slide basket 20 with multiple slides 10 stacked vertically shown below. The arm is retracted and the slide basket 20 is moved in-place. When the desired slide 10 in the basket is aligned vertically to the stage, the insertion arm pushes through the basket and inserts the slide 10 onto the stage. Conversely, the slide 10 is returned to the basket with the slide 10 return arm.

As described earlier, slides 10 must be maintained perpendicular to the optical system to ensure adequate focus. Scanning multiple slides 10 on the stage is especially challenging because orthogonality of the optical system is typically accomplished on a single slide position. Usually by adjusting the tilt of the objective with respect to a calibration slide in a single slide position. In this embodiment or a tray based slide holder, other slide positions are difficult to maintain the desired parallelism to the calibrated slide position. Pockets are typically machined into the stage to hold each slide. Digital Pathology requires parallelism tolerances tighter than standard machining practices and results in poor performance or expensive designs. A more cost-effective method uses metal lapping techniques that provide large surfaces flat to +/−2 um and are typically linear instead of sinusoidal. Meaning, the tolerance is in the form of a sloped line instead of peaks and valleys in the dimensional scale of a specimen slide 10. Consequently, all slides are sloped the same with respect to the perpendicular optical system and can be calibrated orthogonal as described above. Lapping is accomplished by mounting the stage raw material on a table and moving a grinding wheel over the surface to be lapped. This process can only be performed on the upper most surface. This embodiment uses the top, lapped surface of the stage as the reference surface for mounting the slides. All slide holding parts are separate and assembled after lapping.

Although the invention has been explained in relation to its preferred embodiment, it is to be understood that many other possible modifications and variations can be made without departing from the spirit and scope of the invention as hereinafter claimed.

What is claimed is:

1. A slide storage, retrieval, transfer and scanning system for a slide scanner comprising:
   a slide scanning stage configured to receive a slide into a slide holder below a microscope objective and move the slide holder in relation to the microscope objective in order to scan the slide;
   a slide storage assembly configured to store at least one slide basket, wherein each of the at least one slide basket is configured to store a plurality of slides;
   a slide basket transfer assembly configured to retrieve and store the at least one slide basket from and into the slide storage assembly, respectively;
   a slide transfer assembly configured to retrieve a slide from the slide basket transfer assembly, deliver the slide to the slide scanning stage of a slide scanner, and return the slide from the slide scanning stage to the slide basket transfer assembly;
   a slide basket holder of the slide basket transfer assembly being configured to move vertically along a Z axis in order to transfer a slide basket from the slide storage assembly to the slide transfer assembly; and
   a support base of the slide transfer assembly being configured to move horizontally in an X-Y plane in order to transfer a slide from the slide basket transfer assembly to the slide scanning stage of the slide scanner, wherein the Z axis is perpendicular to the X-Y plane.

2. The slide storage, retrieval, transfer and scanning system for a slide scanner as claimed in claim 1 comprising:
   the slide storage assembly comprising a housing, a basket storage carousel, a shaft, and a motor;
   the basket storage carousel being concentrically positioned within the housing;
   the basket storage carousel comprising a plurality of basket storage slots;
   the plurality of basket storage slots being radially positioned around the basket storage carousel;
   the shaft being concentrically connected to the basket storage carousel, wherein the shaft is surrounded by the plurality of basket storage slots;
   the motor being operatively connected to the shaft opposite the basket storage carousel, wherein the motor is operatively connected to the basket storage carousel through the shaft in order to rotate the basket storage carousel within the housing; and
   each of the basket storage slots being configured to removably receive one of the at least one slide basket.

3. The slide storage, retrieval, transfer and scanning system for a slide scanner as claimed in claim 2 comprising:
   each of the at least one slide basket being removably attached within one of the basket storage slots.

4. The slide storage, retrieval, transfer and scanning system for a slide scanner as claimed in claim 2 comprising:
   the housing further comprising a lateral wall and a basket transfer gap traversing through the lateral wall, wherein the basket storage carousel is configured through the motor to radially position a specified basket storage slot from the plurality of basket storage slots adjacent to the basket transfer gap, and wherein a slide basket may be removed from or placed into one of the basket storage slots through the basket transfer gap.

5. The slide storage, retrieval, transfer and scanning system for a slide scanner as claimed in claim 2 comprising:
   each of the plurality of basket storage slots comprising a proximal end and a distal end;
   the proximal end being positioned adjacent the shaft;
   the distal end being positioned adjacent to a lateral wall of the housing; and
   each of the basket storage slots being configured to receive one of the at least one slide basket through the distal end.

6. The slide storage, retrieval, transfer and scanning system for a slide scanner as claimed in claim 2 comprising:
   each of the plurality of basket storage slots comprising a first arm, a second arm, a slot base, a proximal end, and a distal end;
   the slot base being positioned at the distal end;
   the first arm and the second arm being connected perpendicular to the slot base;
   the first arm and the second arm being separated from each other along the slot base; and
   the first arm and the second arm traversing from the slot base to the distal end.

7. The slide storage, retrieval, transfer and scanning system for a slide scanner as claimed in claim 1 comprising:

the slide basket transfer assembly comprising a track and a slide basket holder;
the slide basket holder being configured to move along the track; and
the slide basket holder being configured to removably receive a slide basket.

8. The slide storage, retrieval, transfer and scanning system for a slide scanner as claimed in claim 7 comprising:
the slide basket holder being configured to traverse in a vertical direction along the track.

9. The slide storage, retrieval, transfer and scanning system for a slide scanner as claimed in claim 7 comprising:
the slide basket transfer assembly further comprising a track engagement portion;
the slide basket holder comprising an upper basket holder arm, a lower basket holder arm, and a connecting arm;
the track engagement portion being moveably engaged along the track;
the slide basket holder being connected to the track engagement portion opposite the track;
the lower basket holder arm being terminally and perpendicularly connected to the connecting arm;
the upper basket holder arm being terminally and perpendicularly connected to the connecting arm opposite the lower basket holder arm; and
the slide basket holder being configured to removably receive a slide basket between the upper basket holder arm and the lower basket holder arm.

10. The slide storage, retrieval, transfer and scanning system for a slide scanner as claimed in claim 1 comprising:
the slide transfer assembly comprising a support base, a slide grasping mechanism, and a slide support;
the slide support being positioned on the support base; and
the slide grasping mechanism being integrated onto the support base around the slide support, wherein the slide grasping mechanism is configured to retain a slide on the slide support.

11. The slide storage, retrieval, transfer and scanning system for a slide scanner as claimed in claim 10 comprising:
the slide transfer assembly further comprising:
a motor;
a lip arm;
a fulcrum;
a ramp roller;
a ramp block;
the lip arm being positioned atop the slide support;
the lip arm comprising a proximal lip arm end and a distal lip arm end;
the lip arm being positioned atop the fulcrum;
the fulcrum being positioned between the proximal lip arm end and the distal lip arm end;
the ramp block being connected atop the proximal lip arm end; and
the motor operatively engaged with the ramp roller, wherein the motor is configured to linearly advance the ramp roller up the ramp block in order to raise the distal lip arm end away from the slide support.

12. The slide storage, retrieval, transfer and scanning system for a slide scanner as claimed in claim 1 comprising:
the slide scanning stage comprising:
a slide holder stage;
a slide securing mechanism;
a slide insertion and ejection mechanism;
a Y axis movement mechanism;
an X axis movement mechanism;
the slide holder being positioned on the slide holder stage;
the slide securing mechanism being integrated around the slide holder, wherein the slide securing mechanism secures a slide within the slide holder;
the slide insertion and ejection mechanism being integrated around the slide holder, wherein the slide insertion and ejection mechanism is configured to alternatingly insert the slide into the slide holder and eject the slide from the slide holder; and
the slide holder stage being operatively connected to the X axis movement mechanism and the Y axis movement mechanism, wherein the X axis movement mechanism and the Y axis movement mechanism are jointly configured to move the slide holder stage in an X-Y plane beneath the microscope objective.

13. The slide storage, retrieval, transfer and scanning system for a slide scanner as claimed in claim 12 comprising:
the slide securing mechanism comprising a fixed slide holder and a movable slide holder;
the fixed slide holder and the movable slide holder being positioned laterally opposite each other along the slide holder, wherein the slide is held in place by the fixed slide holder and the movable slide holder; and
the movable slide holder being spring-loaded, wherein compression is applied to the slide by the movable slide holder.

14. The slide storage, retrieval, transfer and scanning system for a slide scanner as claimed in claim 12 comprising:
the slide insertion and ejection mechanism comprising a slide actuation motor, a slide insertion arm, and a slide return arm;
the slide actuation motor being operatively engaged with the slide insertion arm and the slide return arm, wherein the slide insertion arm and the slide return arm move linearly and synchronously with each other through the slide actuation motor; and
the slide insertion arm and the slide ejection arm being positioned opposite each other across the slide holder,
wherein the slide insertion arm presses against the slide in order to insert the slide into the slide holder upon actuation of the slide actuation motor in an insertion direction,
wherein the slide ejection arm presses against the slide in order to eject the slide from the slide holder upon actuation of the slide actuation motor in an ejection direction,
and wherein the ejection direction is the reverse of the insertion direction.

15. The slide storage, retrieval, transfer and scanning system for a slide scanner as claimed in claim 12 comprising:
the slide scanning stage further comprising:
the X axis movement mechanism comprising a X axis movement stage;
the Y axis movement mechanism comprising a Y axis movement stage;
the X axis movement stage being connected to a stage base, wherein the X axis movement stage is configured to move along an X axis atop the stage base;
the Y axis movement stage being connected atop the X axis movement stage, wherein the Y axis movement stage is configured to move along a Y axis atop the X axis movement stage; and the slide holder stage being connected atop the Y axis movement stage.

\* \* \* \* \*